US008831709B2

(12) United States Patent
Intes et al.

(10) Patent No.: US 8,831,709 B2
(45) Date of Patent: Sep. 9, 2014

(54) METHOD FOR 3-DIMENSIONAL FLUORESCENCE TOMOGRAPHIC IMAGING

(75) Inventors: Xavier Intes, Montreal (CA); Frederic Lesage, Montreal (CA); Sirithy Lam, Brest (FR)

(73) Assignee: Softscan Healthcare Group Ltd., Tortola (VG)

( * ) Notice: Subject to any disclaimer, the term of this patent is extended or adjusted under 35 U.S.C. 154(b) by 1911 days.

(21) Appl. No.: 11/576,001

(22) PCT Filed: Sep. 26, 2005

(86) PCT No.: PCT/CA2005/001469
§ 371 (c)(1),
(2), (4) Date: Mar. 31, 2014

(87) PCT Pub. No.: WO2006/032151
PCT Pub. Date: Mar. 30, 2006

(65) Prior Publication Data
US 2008/0260647 A1    Oct. 23, 2008

Related U.S. Application Data

(60) Provisional application No. 60/612,521, filed on Sep. 24, 2004.

(51) Int. Cl.
*A61B 6/00*     (2006.01)
*G01N 21/47*    (2006.01)
*G06T 11/00*    (2006.01)
*G01N 21/64*    (2006.01)
*A61B 5/00*     (2006.01)

(52) U.S. Cl.
CPC ........ *G01N 21/6428* (2013.01); *G01N 21/4795* (2013.01); *G06T 11/006* (2013.01); *G01N 21/6456* (2013.01); *G06T 2211/424* (2013.01); *A61B 5/0073* (2013.01); *A61B 5/0066* (2013.01)
USPC ......... 600/476; 600/407; 600/473; 250/458.1

(58) Field of Classification Search
USPC ........... 600/473, 474, 476, 477, 549; 424/9.6; 250/458.1
See application file for complete search history.

(56) References Cited

U.S. PATENT DOCUMENTS

| 5,577,137 | A | 11/1996 | Groger et al. |
| 2002/0115092 | A1 | 8/2002 | Rebek, Jr. |
| 2002/0136972 | A1* | 9/2002 | Hall et al. ............ 430/82 |
| 2007/0158585 | A1* | 7/2007 | Hall et al. ............ 250/458.1 |

FOREIGN PATENT DOCUMENTS

| CA | 2491748 | 1/2004 |
| EP | 1806999 | 3/2006 |
| WO | 02/41760 | 5/2002 |
| WO | 2005/043138 | 5/2005 |

OTHER PUBLICATIONS

Gao et al. "Improvement of image quality in diffuse optical tomography by use of full time-resolved data". Applied Optics. vol. 41, No. 4, Feb. 1, 2002.*

(Continued)

*Primary Examiner* — Unsu Jung
*Assistant Examiner* — Michael N Fisher
(74) *Attorney, Agent, or Firm* — McCarter & English, LLP.

(57) ABSTRACT

There is provided a method for determining the concentration of a fluorophore in a medium using moments of order k of the fluorescence signal. The method allows higher fidelity 3-dimensional reconstructions of the fluorophore in the medium. The method can be applied in imaging of fluorophores in biological tissues.

11 Claims, 14 Drawing Sheets

(56) References Cited

OTHER PUBLICATIONS

D1 "Time Domain Optical Imaging", Arridge S R; BioMedical Imaging: macro to Nano; 2004, IEEE International Symposium on Arlington, VA, USA , Apr. 15-18, 2004; pp. 1486-1489; XP010774148.

Canadian Office Action issued in Canadian Application No. 2,581,592 on Apr. 18, 2012.

Xingde Li, Dissertation in Physis, U. Penn., Title: Fluorescence and Diffusive Wave Diffraction Tomographic Probes in Turbid Media (1998).

* cited by examiner

FIG_6

“METHOD FOR 3-DIMENSIONAL FLUORESCENCE TOMOGRAPHIC IMAGING

CROSS-REFERENCE TO RELATED APPLICATIONS

This application claims priority on U.S. provisional application 60/612,521 filed Sep. 24, 2004 and entitled METHOD FOR FLUORESCENCE TOMOGRAPHIC IMAGING.

TECHNICAL FIELD

This invention relates to the field of optical characterization and molecular imaging of biological tissues. More specifically the invention relates to the detection of fluorophores in tissues by optical methods.

BACKGROUND OF THE INVENTION

Optical techniques based on the Near-infrared spectral window have made significant progress in biomedical research in recent years. The relative low absorption and low scattering in the 600-1000 nm spectral range allow detection of photons that have traveled through several centimeters of biological tissue [1]. Coupled with accurate models of light propagation, NIR techniques enable imaging of deep tissue with boundary measurements using non-ionizing, low dose radiation.

The interest in NIR techniques is fueled by the ability of the techniques to monitor functional tissue parameter such as oxy- and deoxy-hemoglobin [2] and the development of appropriate low cost instrumentation. Based on these qualities, NIR optical imaging is expected to play a key role in breast cancer detection, characterization [3, 4, 5, 6, 7, 8] and monitoring through therapy [9]; brain functional imaging [10, 11, 12, 13] and stroke monitoring [14, 15]; muscle physiological and peripheral vascular disease imaging [16, 17]. For all these applications, NIR techniques rely on endogenous contrast such as tissue hemodynamics. Another potential application of NIR technique is to monitor exogenous contrast. Especially, we see the emergence of an optical molecular imaging field that bears great promises in clinical applications [18].

NIR fluorescence optical imaging is rapidly evolving as a new modality to monitor functional data in either human or animal tissue. The developments of new contrast agents that target specific molecular events [19, 20, 21] are particularly promising. By specifically binding [22, 23] or being activated in tumors [24], detection can be achieved in the early stages of molecular changes prior to structural modification [25]. Moreover, the endogenous fluorescence in the NIR spectral window is weak leading to exquisite fluorescence sensitivity.

NIR molecular imaging is still confined to small animal models [26] and the translation to human imaging is foreseen as imminent. However, the technical problems encountered in imaging large tissues are challenging. Besides sensitive instrumentation [27], robust and accurate models for fluorescent light propagation are needed. Tomographic algorithms in the continuous mode [28] and in the frequency domain [29, 30] have been proposed. Both numerical and analytical models exist and have been applied successfully to experimental data. However, there is a need for the time-domain algorithms.

SUMMARY OF THE INVENTION

The present invention provides a method that overcomes the deficiencies of the prior art by providing a method to estimate the concentration of a fluorophore as a function of position within an object such as a biological tissue.

In a broad embodiment of the invention expressions for moments of the fluorescence response function are derived and used to reconstruct fluorophore(s) distribution in a volume of interest. In particular the use of higher moments advantageously provide information that is less overwhelmed by the interactions at the surface of the volume.

In one embodiment, the 3-Dimensional (3D) distribution of the fluorophore concentration is recovered by performing a model based inverse problem. In a preferred embodiment there is provided a method for Fluorescent Diffuse Optical Tomography (DOT) expressed within the normalized Born approach. In one aspect the different moments of the Time Point Spread Function (TPSF) are analytically derived to construct the forward model. Enhanced performance of fluorescence DOT was achieved using these new analytical solutions when compared to current formulations.

BRIEF DESCRIPTION OF THE DRAWINGS

Further features and advantages of the present invention will become apparent from the following detailed description, taken in combination with the appended drawings, in which.

DETAILED DESCRIPTION OF THE PREFERRED EMBODIMENT

Figure 1:
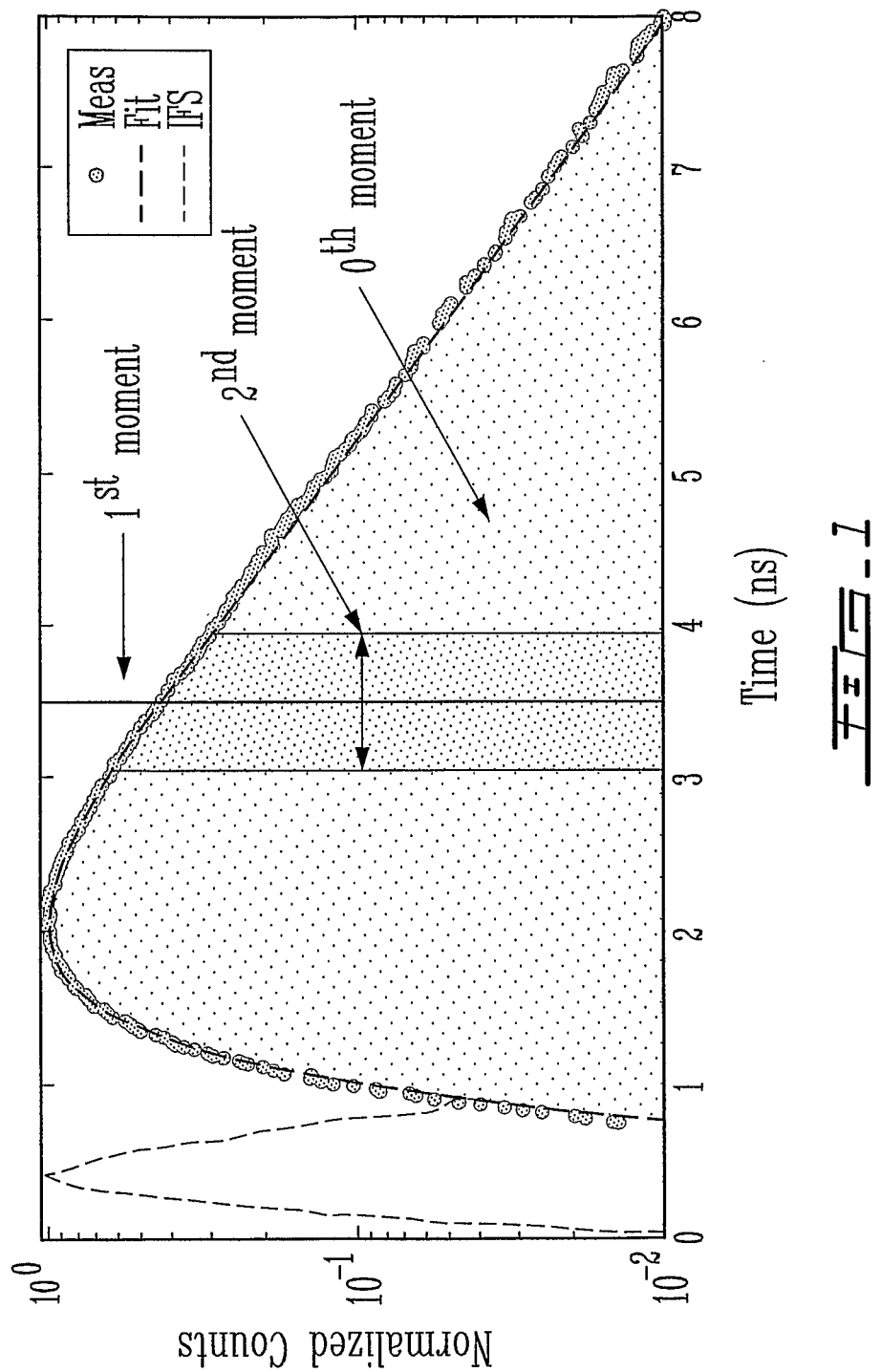
FIG. 1 is a typical TPSF and respective moments.

Light propagation in tissue is well modeled by the diffusion equation. In the time domain the mathematical expression modeling light propagation in a homogenous medium is:

$$\frac{1}{v}\frac{\partial}{\partial t}\Phi(r, t) - D\nabla^2\Phi(r, t) + \mu_a\Phi(r, t) = S(r, t) \qquad (1)$$

Where $\Phi(r,t)$ is the photon fluence rate, D is the diffusion coefficient expressed as $D=1/3\mu_s'$, with $\mu_s'$ being the scattering coefficient, $\mu_a$ is the linear absorption coefficient, v is the speed of light in the medium and $S(r,t)$ is the source term (assumed to be a $\delta$ function in our case). It will be appreciated that other expressions for modeling light propagation, such as the radiation transfer equation, can be used as would be obvious to one skilled in the art. Also the light propagation can be modeled numerically or using techniques such as Monte Carlo simulations again the person skilled in the art would be familiar with these techniques.

From equation (1), we can estimate the value of the field in each position in the investigated medium. In turn, the knowledge of the value of the field locally allows modeling accurately the reemission of a fluorescent field by endogenous or exogenous markers such as fluorophores. Indeed, the fluorescent field is due to excited molecules that reemit photons at a constant wavelength. This phenomenon of reemission can be modeled as source term embedded in the medium and the propagation from these sources to the detector, modeled in the same frame as in equation (1).

The temporal behavior of the excited population at a given point is expressed by [31]:

$$\frac{\partial}{\partial t}N_{ex}(r, t) = -\frac{1}{\tau}N_{ex}(r, t) + \sigma \cdot \Phi^{\lambda 1}(r, t)[N_{tot}(r, t) - 2n_{ex}(r, t)] \qquad (2)$$

where $N_{ex}(r,t)$ is the concentration of excited molecules at position r and time t, $N_{tot}(r,t)$ is the concentration of total molecules of fluorophores (excited or not), $\tau$ is the radiative lifetime of the fluorescent compound (sec. or nanoseconds), $\sigma$ is the absorption cross section of the fluorophore (cm$^2$) and $\Phi^{\lambda 1}(r,t)$ is the photon fluence rate (number of photons s$^{-1}$ cm$^{-2}$) at the excitation wavelength $\lambda_1$. Considering that the number of excited molecule is low compared to the total molecules and working in the frequency domain yields the expression for the concentration of excited molecules:

$$N_{ex}(r, \omega) = \frac{\sigma \cdot N_{tot}(r)}{1 - i\omega\tau} \cdot \Phi^{\lambda 1}(r, \omega) \qquad (3)$$

where $\omega_1$ is the angular frequency at the excitation wavelength $\lambda_1$. The time domain and the frequency domain are linked through Fourier transform. Therefore the above derivation can also be used for fluorescence measurements performed in the time-domain. Furthermore the time domain may also be linked to continuous wave (CW) measurements by integration of the total temporal point spread function (TPSF).

Then, the total fluorescent field is the sum of the contributions of all the secondary fluorescent sources over the entire volume. In the case of a point source located at $r_s$, the fluorescent field detected at a position $r_d$, is modeled by:

$$\Phi^{\lambda 2}(r_s, r_d, \omega) = \eta\iiint_{volume} N_{ex}(r, \omega) \cdot \Phi^{\lambda 2}(r, r_d, \omega) \cdot d^3r \qquad (4)$$

where $\Phi^{\lambda 2}(r,r_d,\omega_2)$ represent a propagation term of the fluorescent field from the element of volume at r to the detector position $r_d$ at the reemission wavelength $\lambda_2$. Then, by using equation (4) we obtain the fluorescent term:

$$\Phi^{\lambda 2}(r_s, r_d, \omega) = \iiint_{volume} \Phi^{\lambda 1}(r_s, r, \omega) \cdot \frac{Q_{eff} \cdot N_{tot}(r)}{1 - i\omega\tau} \cdot \Phi^{\lambda 2}(r, r_d, \omega) \cdot d^3r \qquad (5)$$

Where $Q_{eff}=q\cdot\eta$. $\sigma$ is the quantum efficiency, product of q the quenching factor, $\eta$ the quantum yield and $\sigma$ absorption cross section of the fluorophore. Note that the product $\sigma N_{tot}(r)$ corresponds to the absorption coefficient of the fluorophore and can also be expressed as $\epsilon C_{tot}(r)$ where $\epsilon$ is the extinction coefficient (cm$^{-1}$ Mol$^{-1}$) and $C_{tot}(r)$ is the concentration of the fluorophore at position r.

Following the derivation of equation (5) performed by Xingde Li [31, incorporated herein by reference], Ntziachristos and Weissleder [28, incorporated herein by reference] proposed a cost efficient mathematical approach to fluorescent diffuse optical tomography. They cast the forward model in the frame of the normalized first order Born approximation that is mathematically expressed as:

$$\frac{\Phi^{\lambda 2}(r_s, r_d, \omega)}{\Phi^{\lambda 1}(r_s, r_d, \omega)} = \qquad (6)$$

$$\frac{1}{\Phi_0^{\lambda 1}(r_s, r_d, \omega)}\iiint_{volume} \Phi_0^{\lambda 1}(r_s, r, \omega) \cdot \frac{Q_{eff} \cdot C_{tot}(r)}{1 - i\omega\tau} \cdot \Phi_0^{\lambda 2}(r, r_d, \omega) d^3r$$

Figure 15:
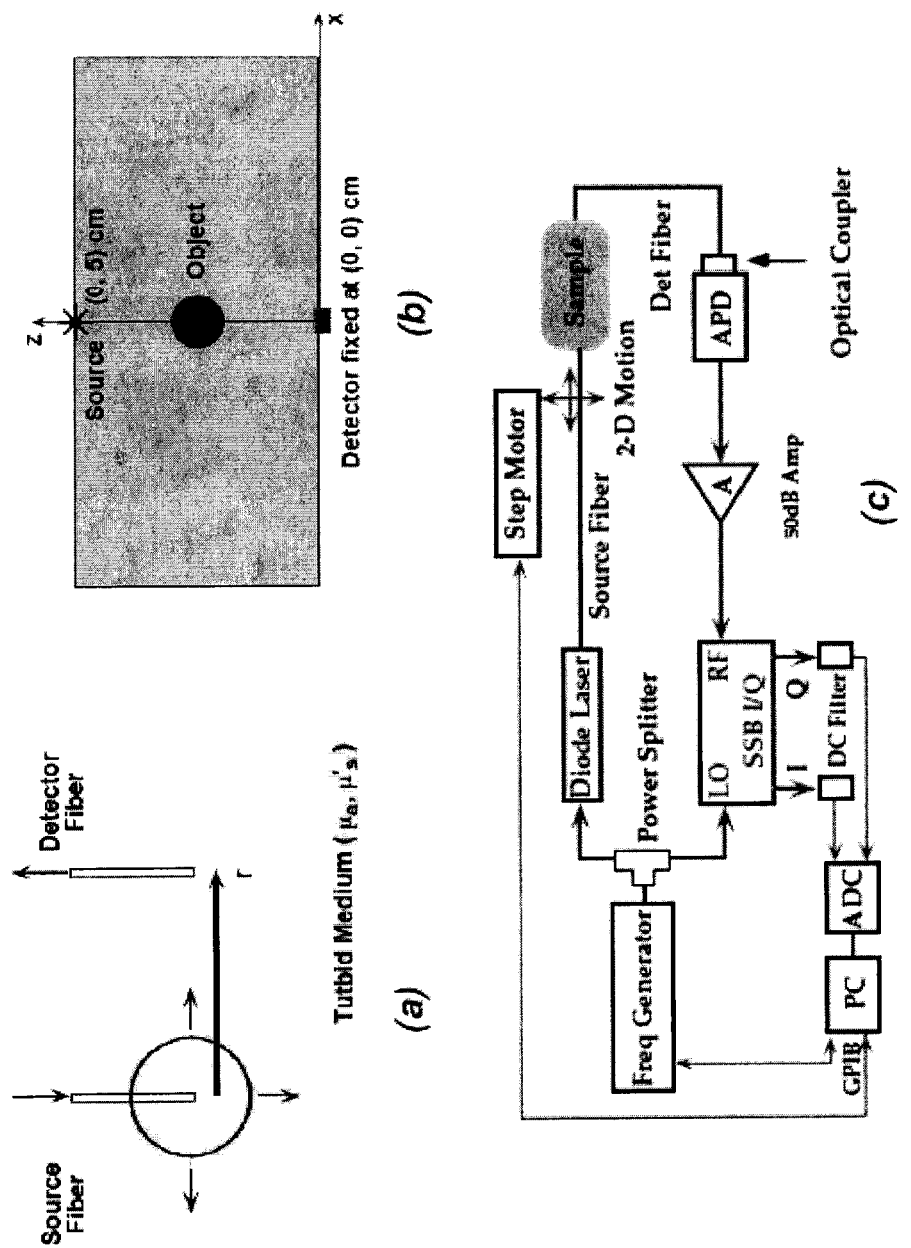
FIG. 15 is a schematic representation of a various geometries using source-detector pairs.

Xingde Li [31] describes an infrared optical technique. FIG. 15 is a schematic representation of a various geometries using source-detector pairs. The Figure reproduces some of Li's schematics. FIG. 15A shows a pair formed of a source fiber and a detector fiber, in which a source-detector geometry is arranged so that a directional photon flux r is perpendicular to a detector surface. FIG. 15B shows another source-detector configuration in which a detector is shown a position indicated as (0,0) cm along a plane formed by axes x and y, while a source is positioned at (0,5) cm on the same plane. An object to be imaged by fluorescence technique is located between the pair formed by the source and detector. FIG. 15C shows a block diagram of a setup including a source formed of a diode laser coupled with a source fiber and a detector fiber optically coupled with an avalanche photo diode (APD). A sample is placed between the source-detector pair. A step motor moves the source in a 2-dimensional plane. A single side band (SSB) in-phase/quadrature-phase (I/Q) demodulator connected to the APD receives a signal from the detector, via an amplifier (A), on a radiofrequency (RF) port. I and Q outputs of the demodulator are filtered by direct current (DC) filters and converted by an analog to digital converter (ADC) before being applied to a computer (PC). The PC controls a frequency generator and the step motor. A power splitter directs an output of the frequency generator to both the diode laser and a local port (LO) of the demodulator. A general purpose interface bus (GPIB) relays digital signals.

The difference between equation (5) and (6) resides in the normalization achieved with the homogeneous excitation field reaching the detector. Following the expression of M. O'Leary [32, incorporated herein by reference], this expression is used to construct the forward model for diffuse optical tomography (DOT) and then the $$\frac{\Phi^{\lambda 2}(r_s, r_d, \omega)}{\Phi^{\lambda 1}(r_s, r_d, \omega)} = \frac{D^{\lambda 1}}{G(r_s, r_d, \omega)} \sum_{voxels} \frac{1}{D^{\lambda 1}} G^{\lambda 1}(r_s, r_v, \omega) \cdot \qquad (7)$$

$$\frac{Q_{eff} \cdot C_{tot}(r_v)}{1 - i\omega\tau} \cdot \frac{1}{D^{\lambda 2}} G^{\lambda 2}(r_v, r_d, \omega) h^3.$$

where $$G^{\lambda j}(r_1, r_2, \omega) = \frac{e^{(ik_j|r_1 - r_2|)}}{|r_1 - r_2|}$$

is the system's Green function with $k^2 = (-v\mu^{\lambda j}_a + i\omega)/D^{\lambda j}$ at the considered wavelength $\lambda_j \in (\lambda_1, \lambda_2)$.

The expression of equation (7) is defined in the frequency domain. In one embodiment of the present invention analytical solutions in the time domain are provided. Such analytical solutions for the absorption case have been proposed in the past for the $0^{th}$, $1^{st}$ and $2^{nd}$ moment of the TPSF [33]. The correspondence of these moments to the TPSF is illustrated in FIG. 1. The $0^{th}$ moment corresponds to the integration of the counts (equivalent to the continuous wave mode), the $1^{st}$ moment corresponds to the mean time of arrival of the photon and the $2^{nd}$ moment to the variance of arrival of the photon.

The normalized moments of order k of a distribution function p(t) are defined by [34];

$$m_k = \langle t^k \rangle = \int_{-\infty}^{+\infty} t^k \cdot p(t) dt \Big/ \int_{-\infty}^{+\infty} p(t) dt \qquad (8)$$

We employed this formalism in the case of the normalized first order Born approximation. Hence the normalized $0^{th}$ moment is expressed as:

$$m_0^{\lambda 2}(r_s, r_d) = \Phi_N^{\lambda 2}(r_s, r_d, \omega = 0) \qquad (9)$$

$$= \sum_{voxels} \frac{G^{\lambda 1}(r_s, r_v, \omega = 0) \cdot G^{\lambda 2}(r_v, r_d, \omega = 0)}{G^{\lambda 1}(r_s, r_d, \omega = 0)} \times$$

$$\frac{Q_{eff} h^3}{D_2} \times C_{tot}(r_v)$$

This expression is equivalent to equation (7) for the continuous mode. Then normalizing the $1^{st}$ and the $2^{nd}$ moment to this first moment yields the analytical solutions:

Normalized $1^{st}$ moment $$m_0^{\lambda 2}(r_s, r_d) \cdot m_1^{\lambda 2}(r_s, r_d) = \qquad (10)$$

$$\sum_{voxels} \left\{ \frac{\left(\tau + \frac{|r_s - r_v| - |r_s - r_d|}{2 \cdot v\sqrt{\mu_a D_1}} + \frac{|r_v - r_d|}{2 \cdot v\sqrt{\mu_a D_2}}\right) \times}{\frac{G^{\lambda 1}(r_s, r_v, \omega = 0) \cdot G^{\lambda 2}(r_v, r_d, \omega = 0)}{G^{\lambda 1}(r_s, r_d, \omega = 0)} \times \frac{Q_{eff} h^3}{D_2} \times C_{tot}(r_v)} \right\}$$

Normalized $2^{nd}$ moment $$m_0^{\lambda 2}(r_s, r_d) \cdot m_2^{\lambda 2}(r_s, r_d) = \qquad (11)$$

$$\sum_{voxels} \left\{ \begin{array}{l} \left( \tau^2 + \frac{|r_s - r_v| - |r_s - r_d|}{4 \cdot v^2 \mu_a \sqrt{\mu_a D_1}} + \frac{|r_v - r_d|}{4 \cdot v^2 \mu_a \sqrt{\mu_a D_2}} + \right. \\ \left\{ \tau + \frac{|r_s - r_v|}{2 \cdot v\sqrt{\mu_a D_1}} + \frac{|r_v - r_d|}{2 \cdot v\sqrt{\mu_a D_2}} \right\}^2 - \bar{t}^{\lambda 2}(r_s, r_d) \cdot \\ \left\{ \tau + \frac{|r_s - r_v| + |r_v - r_d|}{2 \cdot v\sqrt{\mu_a D_1}} + \frac{|r_v - r_d|}{2 \cdot v\sqrt{\mu_a D_2}} \right\} \\ \frac{G^{\lambda 1}(r_s, r_v, \omega = 0) \cdot G^{\lambda 2}(r_v, r_d, \omega = 0)}{G^{\lambda 1}(r_s, r_d, \omega = 0)} \times \frac{Q_{eff} h^3}{D_2} \times C_{tot}(r_v) \end{array} \right\}$$

Where $\bar{t}^{\lambda 2}(r_s, r_d)$ corresponds to the fluorescent mean time for the particular source-detector pair considered.

In one embodiment of the invention the fluorescent Diffuse Optical Tomography (DOT) problem in time domain is based on the analytical expression derived above and summarized in the linear set of equations:

$$\begin{vmatrix} m_0^{\lambda 2}(r_{s1}, r_{d1}) \\ \vdots \\ m_0^{\lambda 2}(r_{sm}, r_{dm}) \\ \hline m_0^{\lambda 2}(r_{s1}, r_{d1}) \cdot m_1^{\lambda 2}(r_{s1}, r_{d1}) \\ \vdots \\ m_0^{\lambda 2}(r_{sm}, r_{dm}) \cdot m_1^{\lambda 2}(r_{sm}, r_{dm}) \\ \hline m_0^{\lambda 2}(r_{s1}, r_{d1}) \cdot m_2^{\lambda 2}(r_{s1}, r_{d1}) \\ \vdots \\ m_0^{\lambda 2}(r_{sm}, r_{dm}) \cdot m_2^{\lambda 2}(r_{sm}, r_{dm}) \end{vmatrix} = \begin{vmatrix} W_{11}^{m_0^{\lambda 2}} & \cdots & W_{1n}^{m_0^{\lambda 2}} \\ \vdots & \ddots & \vdots \\ W_{m1}^{m_0^{\lambda 2}} & \cdots & W_{mn}^{m_0^{\lambda 2}} \\ \hline W_{11}^{m_0^{\lambda 2} \cdot m_1^{\lambda 2}} & \cdots & W_{1n}^{m_0^{\lambda 2} \cdot m_1^{\lambda 2}} \\ \vdots & \ddots & \vdots \\ W_{m1}^{m_0^{\lambda 2} \cdot m_1^{\lambda 2}} & \cdots & W_{mn}^{m_0^{\lambda 2} \cdot m_1^{\lambda 2}} \\ \hline W_{11}^{m_0^{\lambda 2} \cdot m_2^{\lambda 2}} & \cdots & W_{1n}^{m_0^{\lambda 2} \cdot m_2^{\lambda 2}} \\ \vdots & \ddots & \vdots \\ W_{m1}^{m_0^{\lambda 2} \cdot m_2^{\lambda 2}} & \cdots & W_{mn}^{m_0^{\lambda 2} \cdot m_2^{\lambda 2}} \end{vmatrix} \cdot \begin{vmatrix} C_{tot}(r_{v1}) \\ \vdots \\ \vdots \\ \vdots \\ \vdots \\ \vdots \\ C_{tot}(r_{vn}) \end{vmatrix} \qquad (12)$$

Where $W_{ij}^{m_0^{\lambda 2}}$, $W_{ij}^{m_0^{\lambda 2} \cdot m_1^{\lambda 2}}$ and $W_{ij}^{m_0^{\lambda 2} \cdot m_2^{\lambda 2}}$, the weight function for the $i^{th}$ source-detector pair and the $j^{th}$ voxel are directly derived respectively from equations (9), (10) and (11). In this inverse problem, the object function is defined as the fluorophore concentration.

It will be appreciated from the above that the concentration can be estimated using one or more moments.

For the cases presented herein, boundary conditions were implemented using the extrapolated boundary conditions [35, incorporated herein by reference].

Many different approaches exist to tackle the inverse problem [36] such as singular value decomposition, conjugate gradient and the like. In a preferred embodiment, the algebraic reconstruction technique (ART) was used due to its modest memory requirements for large inversion problems and the calculation speed it attains.

Algebraic techniques are well known and broadly used in the biomedical community [37]. These techniques operate on a system of linear equations such as the ones seen in equation (12). We can rewrite equation (12) as:

$$b = A \cdot x \quad (13)$$

where b is a vector holding the measurements for each source-detector pair, A is the matrix of the forward model (weight matrix), and x is the vector of unknowns (object function). ART solves this linear system by sequentially projecting a solution estimate onto the hyperplanes defined by each row of the linear system. The technique is used in an iterative scheme and the projection at the end of the $k^{th}$ iteration becomes the estimate for the $(k+1)^{th}$ iteration. This projection process can be expressed mathematically as [38]:

$$x_j^{(k+1)} = x_j^{(k)} + \lambda \frac{b_i - \sum_i a_{ij} x_j^{(k)}}{\sum_i a_{ij} a_{ij}} \sum_i a_{ij} \quad (14)$$

where $x_j^{(k)}$ is the $k^{th}$ estimate of $j^{th}$ element of the object function, $b_i$ the $i^{th}$ measurement, $a_{ij}$ the i-$j^{th}$ element of the weight matrix A and $\lambda$ the relaxation parameter.

The relaxation parameter adjusts the projection step for each iterations. A small $\lambda$ value makes the inversion more robust but also slows conversion. The selection of $\lambda$ can be done empirically [39, 40, 41, 42, incorporated herein by reference]. We have set $\lambda = 0.1$ based on previous studies [43]. Also, a positive constraint was imposed on the object function. This hard constraint is adequate with fluorescent measurement as long as negative concentrations are unphysical. For a typical case such as displayed in FIG. 3 where we have $N_{meas} = 81 \times 3$ and $N_{vox} = 17928$, the reconstruction was performed in ~6 min on a with 512 Mb ram-600 MHz Pentium III.

It will be appreciated that the data can be acquired in the Frequency Domain at several frequencies to reconstruct the TPSF via the Fourier Transform.

EXAMPLES

Example 1

Photon propagation is often referred to as a banana shape. Especially, in the case of continuous mode, the measurements are highly sensitive to the surface. Such dependence of the data type can be visualized through the mapping of the sensitivity matrix. Indeed, each line of the linear system described in equation (12) represents the dependence to a local perturbation for the corresponding source-detector pair. Thus by mapping this local dependence, we render the spatial sensitivity of this particular source-detector pair for this specific configuration and specific data type.

Figure 2:
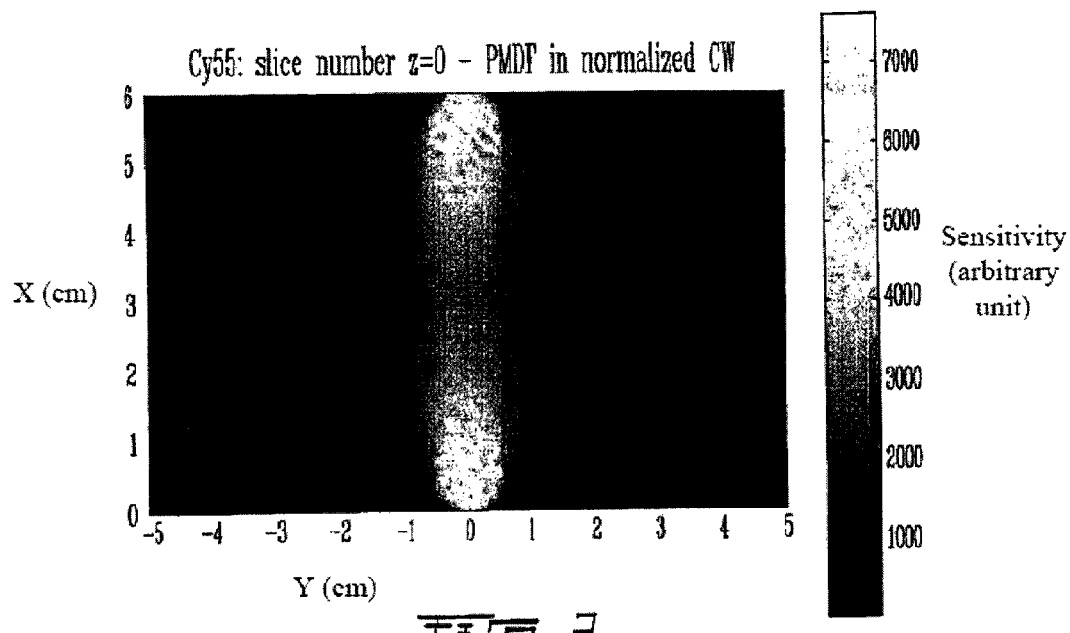
FIG. 2 is an example of a sensitivity matrix for $m_0^{\lambda_2}$ and for a 6 cm thick slab with source-detector facing each other and in which the background fluorochrome was set to 0.1 μM of Cy 5.5 (τ=1 ns)
Figure 3:
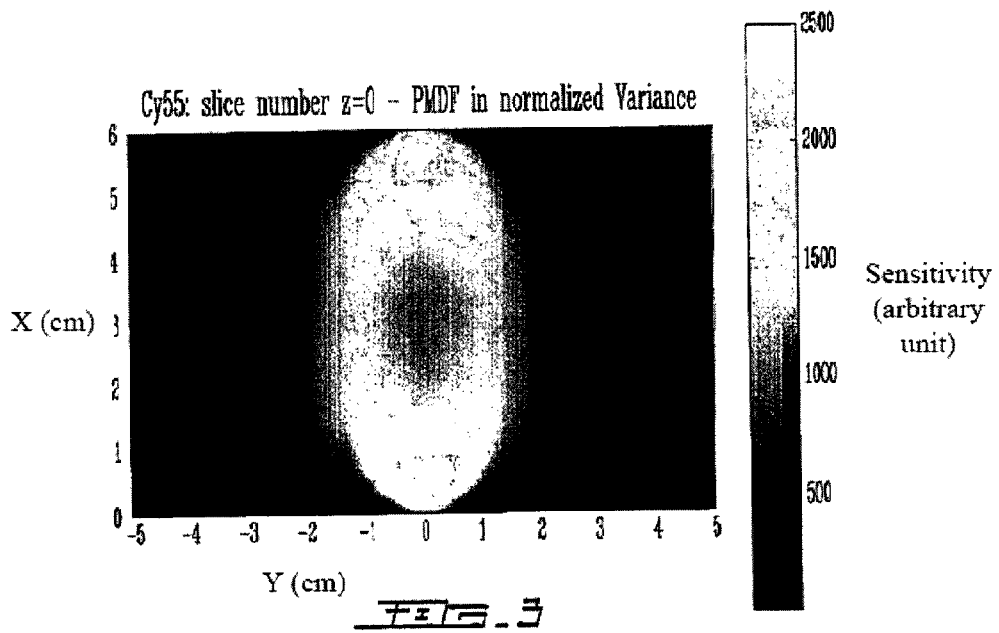
FIG. 3 is an example of a sensitivity matrix for $m_0^{\lambda_2} \cdot m_2^{\lambda_2}$ for the same set up as in FIG. 2.
Figure 4:
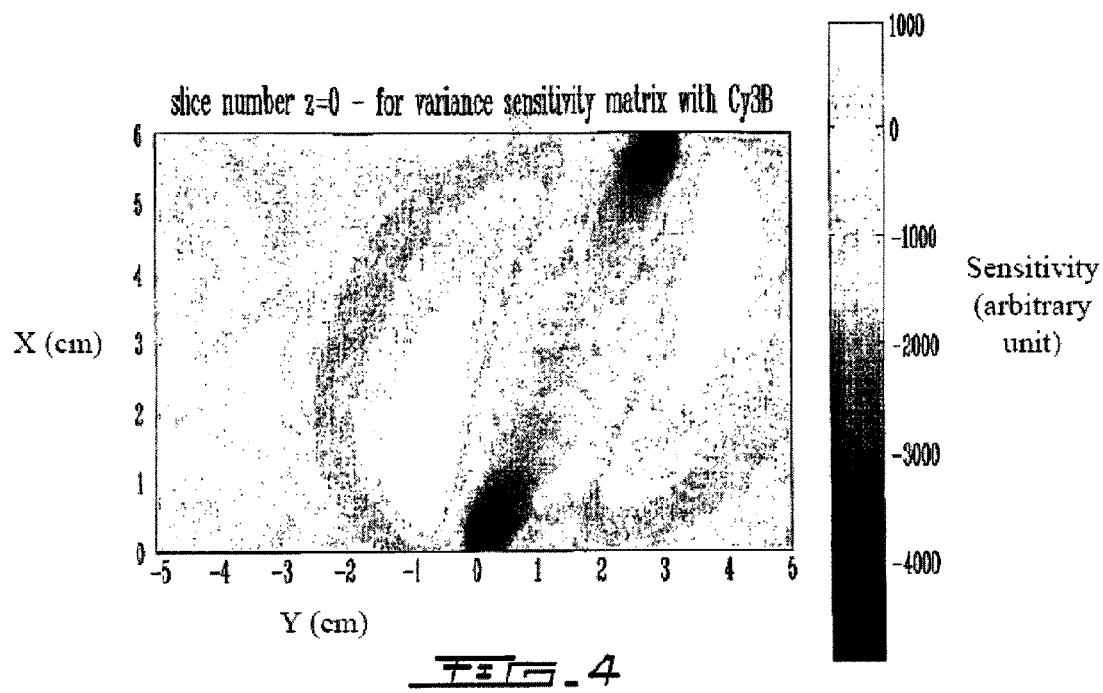
FIG. 4 is an example of a sensitivity matrix for $m_0^{\lambda_2} \cdot m_2^{\lambda_2}$ for a source-detector pair in transmittance geometry but not facing each other in which the background fluorochrome was set to 0.1 μM of Cy 7 (τ=0.3 ns)

Some examples of sensitivity matrix for relevant cases are shown in FIGS. 2, 3 and 4. Slices are depicted but by construction, the banana shapes are in 3D.

First, as seen in FIG. 2, the normalized first order Born approximation in continuous mode is highly sensitive to surface voxels. This is a well-known behavior that is both present in absorption and fluorescent mode. This also demonstrates the poor sensitivity of planar fluorescent techniques to deep fluorescent inclusions due to overwhelming dependence on surface interactions. On this and later Figures, fluorophore positions are presented in a 3D space along arbitrary axes X, Y and Z.

Secondly, we see that the spatial dependence profile of the $2^{nd}$ normalized fluorescent moment (FIG. 3) possess distinctive features. The $2^{nd}$ normalized fluorescent moment still exhibits some strong dependence from the surface voxels, but also from deeper voxel. The profile presents a distinguishing depression in the line connecting the source detector pair. This fact is striking in the case of FIG. 4 where we used the properties of Cy 3B for the simulated chromophore. In this specific case, the $2^{nd}$ normalized fluorescent moment is characterized by a sharp and well-demarcated hollow dependence. Such typical features are related to the fact the fluorescent mean time $\bar{t}^{\lambda,2}(r_s, r_d)$ is subtracted in equation (11). Indeed, the measured mean-time is always greater than the mean time of propagation for the shorter path, i.e. for the voxels located on the line connecting the source-detector pair. Then if the contribution of the lifetime is small enough, the $2^{nd}$ normalized fluorescent moment will exhibit reduced (eventually negative) contribution for these voxels.

From this set of examples, we note that the $2^{nd}$ normalized fluorescent moment provide a different kind of information compare to the $0^{th}$ normalized moment of the fluorescent TPSF (we overlooked here the $1^{st}$ moment for simplicity). The incorporation of this additional information in fluorescent DOT is expected to produce more accurate reconstructions.

We tested the formulation derived above with simulations of 3D reconstructions. First we constructed a synthetic phantom with parameters relevant to the human breast in dimension and for the optical endogenous properties. Second we simulated a homogeneous fluorochrome distribution over the volume with a 1 cm³ single inclusion embedded in the middle of the volume and exhibiting a contrast of 10 in concentration. The different parameters of the simulations are provided in Table 1.

TABLE 1

Parameters used in the simulation.

| | | | |
|---|---|---|---|
| $\mu_a^{\lambda 1}$ (cm$^{-1}$) | 0.06 | $C_{background}$ (μM/L) | 0.1 |
| $\mu_s^{\lambda 1}$ (cm$^{-1}$) | 10.00 | $C_{inclusion}$ (μM/L) | 1.0 |
| $\mu_s^{\lambda 2}$ (cm$^{-1}$) | 10.00 | τ (ns) | 1.0 |
| Dimensions (cm) | 10 × 6 × 10 | ε (cm$^{-1}$ · M$^{-1}$) | 190,000 |
| Voxel size (cm) | 0.3 × 0.3 × 0.3 | η (%) | 0.23 |

Figure 5:
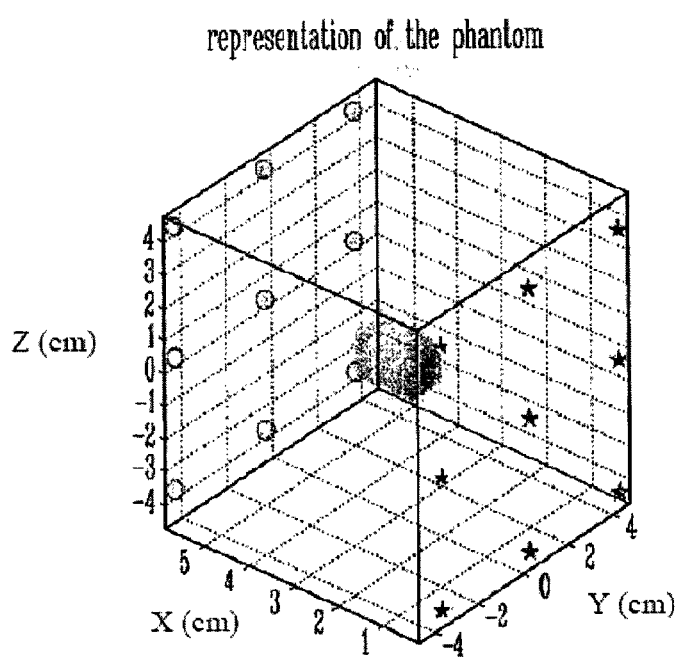
FIG. 5 is a representation of the phantom simulated.
Figure 6:
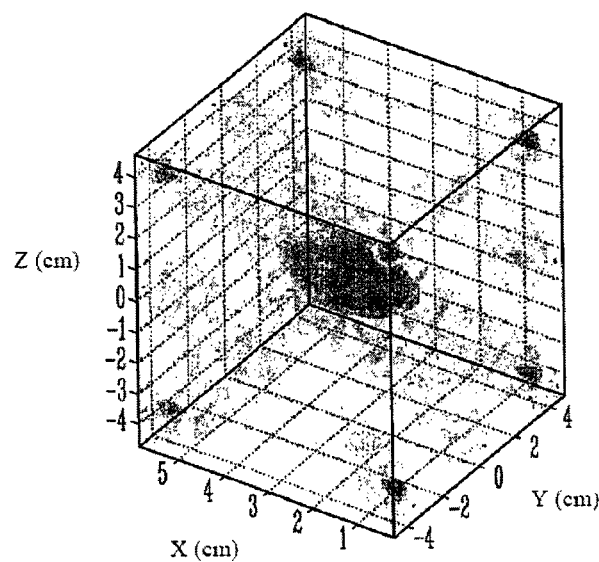
FIG. 6 is a reconstructed phantom with values based on the $0^{th}$ moment only in which the number of iterations in the ART algorithm was set to 100.
Figure 7:
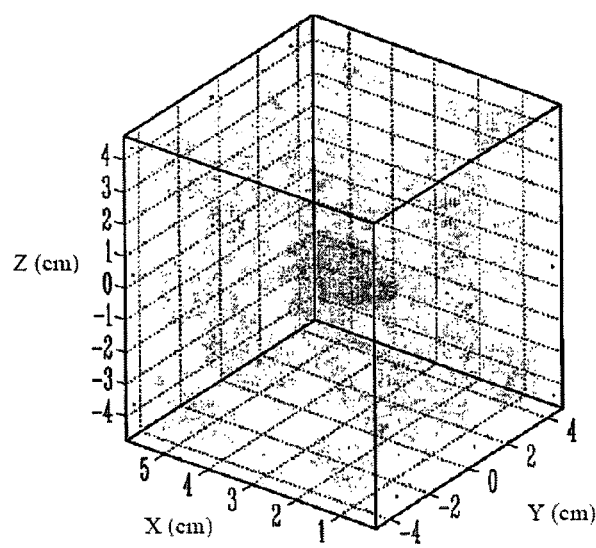
FIG. 7 is a reconstructed phantom with values based on the $2^{nd}$ moment only in which the number of iterations in the ART algorithm was set to 200.
Figure 8:
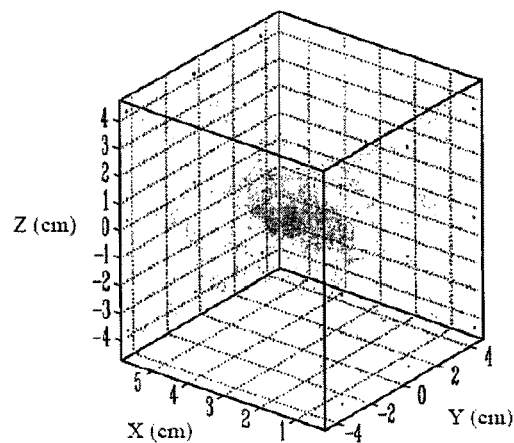
FIG. 8 is a reconstructed phantom with values based on the $0^{th}$, $1^{st}$ and $2^{nd}$ moments in which the number of iterations in the ART algorithm was set to 200.

We use then the formulation of (12) to generate synthetic measurements from the phantom. We simulated an array of nine sources and nine detectors as described in FIG. 5. The value of the fluorescent mean time and the fluorescent variance were evaluated to be around ~3 ns and 1 ns respectively. These values are in agreement with expected values for real cases. In this simulation no noise was added. The reconstructions obtained by constrained ART are provided in FIGS. 6, 7 and 8. We propose in these figures the reconstructions based on the $0^{th}$ normalized moment of the fluorescent TPSF, $2^{nd}$ normalized fluorescent moment and with the combined three normalized moments.

In all three cases presented, the inclusion was successfully reconstructed. Its location was well retrieved and the object clearly discriminated from the background. However, we can notice some differences in term of reconstruction quality between the three different inverse problems solved. Especially, in the case of normalized moment of the fluorescent TPSF only, the reconstructions exhibitstrong artifacts on the boundary, artifacts that scale with the reconstructed heterogeneity. While the reconstructions based on the $2^{nd}$ normalized fluorescent moment reducethe surface artifacts compared to the reconstruction based on the $0^{th}$ moment. In this case, the homogenous background fluorophore is more accurately reconstructed. When the three moments are incorporated in the inverse problem, the gain is even more appreciable.

These findings are related to the results described above. For the $0^{th}$ normalized moment reconstructions, due to the high sensitivity to surface voxels, artifacts placed in front of the individual source and detectors are expected. Especially in our case where a non-negligible fluorophore homogeneous background concentration was simulated. The contribution of this homogenous background to the measurements is reconstructed as a strong concentration localized in front of the optodes. Reconstructions based on the $2^{nd}$ normalized fluorescent moment donot suffer as much from this ambiguity. The reconstruction does not exhibit artifacts scaling with the reconstructed heterogeneity. Moreover, the homogeneous background is reconstructed with more fidelity. The gain is even more substantial when the three moments are used simultaneously in the inverse problem. In this case, the object is accurately reconstructed in location and size with a more homogeneous background fluorophore concentration.

While the reconstruction is provided in three dimension, the method can be used to assess the concentration as a function of one coordinate only. In a preferred embodiment this coordinate is the depth relative to a surface of the object in which the fluorophore is embedded. This may be accomplished, for example, by considering a region of interest as a unique voxel resolved in one dimension only.

The method for estimating the concentration of fluorophores described above can be applied to biological tissues such as brain and breast tissue. The fluorophore can be endogenous or exogenous and the concentration of several fluorophores may be determined simultaneously when using multiple excitation and emission wavelengths.

The reconstructions presented in this section highlight the benefit of the time domain normalized moments formulation over the traditional $0^{th}$ normalized moment. The higher moment of the fluorescent TPSF provides information that is less overwhelmed by the surface interactions. The gain is important when a background fluorophore concentration exists, as it is generally the case in molecular imaging. Strong surface concentrations that are generally considered as plaguing artifacts in continuous wave fluorescent imaging are avoided in reconstruction with higher moments or their combination when a background fluorophore distribution exists.

Example 2

A synthetic phantom with parameters relevant to the softly compressed human breast in dimension (6 cm thickness) and for the optical endogenous properties was constructed. Then we simulated a homogeneous fluorochrome distribution over the volume with 1 cm$^3$ heterogeneities exhibiting a contrast of 10 in concentration. The different parameters of the simulations are provided in Table 2.

The fluorescent signal is dependent on the intrinsic characteristics of the fluorochrome employed. Simulations were carried out with three representative compounds: Cy 7, Cy 5.5 and Cy 3B. These fluorochromes were selected due to the span of lifetimes they do exhibit, which is characteristic of cyanine dyes (Zheng et al. J. Porphyrin and Phthalocyanines 8, 1106-1118 (2004)). The different properties of these fluorochromes are provided in Table 3.

TABLE 2

Parameters used in the simulations.

| | | | |
|---|---|---|---|
| $\mu_a^{\lambda 1}$ (cm$^{-1}$) | 0.06 | Dimensions (cm) | 9 × 6 × 9 |
| $\mu_a^{\lambda 2}$ (cm$^{-1}$) | 0.06 | $C_{background}$ (µM) | 0.1 |
| $\mu_s'^{\lambda 1}$ (cm$^{-1}$) | 10.00 | $C_{inclusion}$ (µM) | 1.0 |
| $\mu_s'^{\lambda 2}$ (cm$^{-1}$) | 10.00 | Voxel size (cm) | 0.36 × 0.3 × 0.36 |

Figure 9:
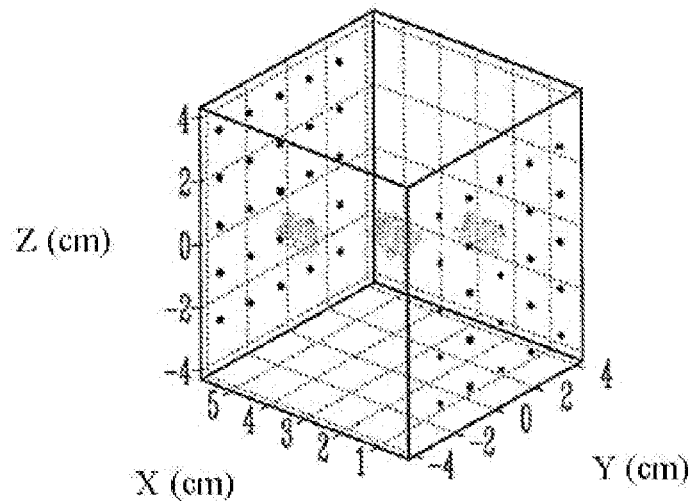
FIG. 9 is a configuration used for the simulations in which the source (detectors) locations are depicted by dots.
Figure 10:
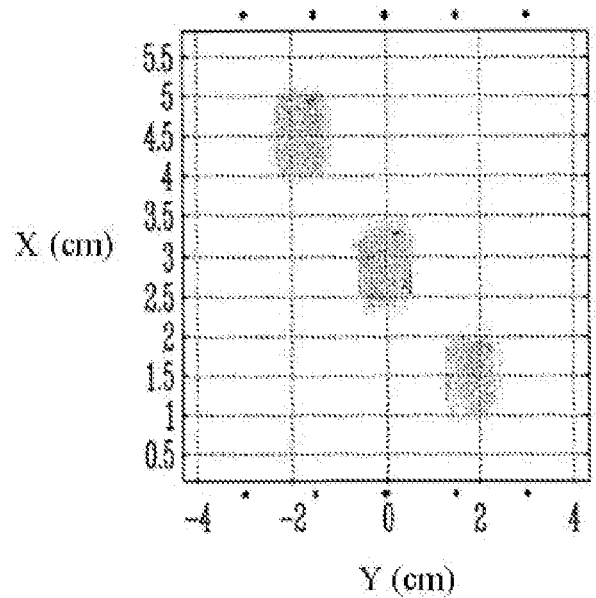
FIG. 10 is a configuration used for the simulations in which the source (detectors) locations are depicted by dots.

The synthetic phantom was probed with a 25×25 constellation of source detectors. This constellation was distributed evenly 1.5 cm apart in both dimensions. The phantom configuration is provided in FIG. 9.

TABLE 3

Fluorochrome investigated herein.

| Compound | τ (ns) | ε (cm$^{-1}$ · M$^{-1}$) | η (%) |
|---|---|---|---|
| Cy 7 | <0.3 | 200 000 | 0.28 |
| Cy 5.5 | 1.0 | 190 000 | 0.23 |
| Cy 3-B | 2.8 | 130 000 | 0.67 |

Higher order moments are sensitive to noise. Thus, the performance of the algorithm in the presence of noise can be evaluated. Analytical noise models exist for the intrinsic NIR higher moments for homogeneous cases (Liebert et al. Appl. Opt. 42, 5785). However, the derivation of the same analytical model for tomographic purposes is overly complex. We decided thus to employ a heuristically derived noise model.

Figure 11A:
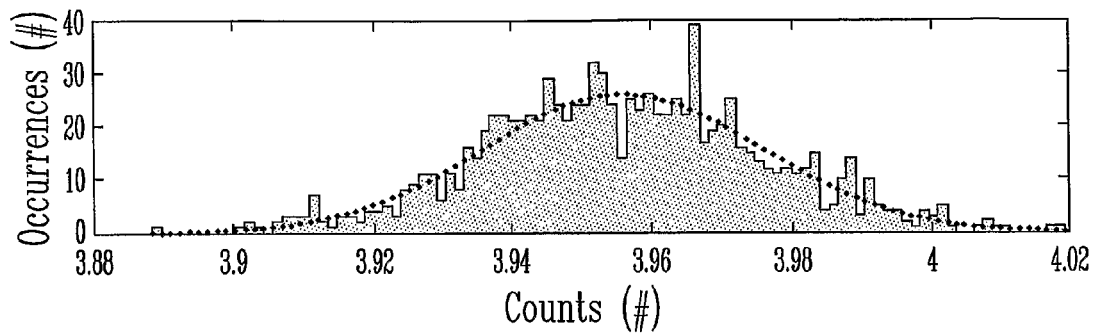
FIG. 11 shows the results of repartition of energy, mean times and variance of 1,000 randomly generated noised TPSF.
Figure 11B:
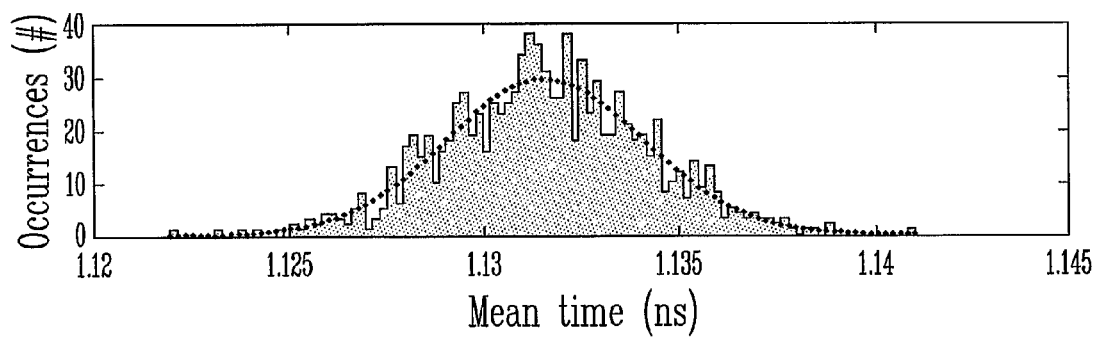
Figure 11C:
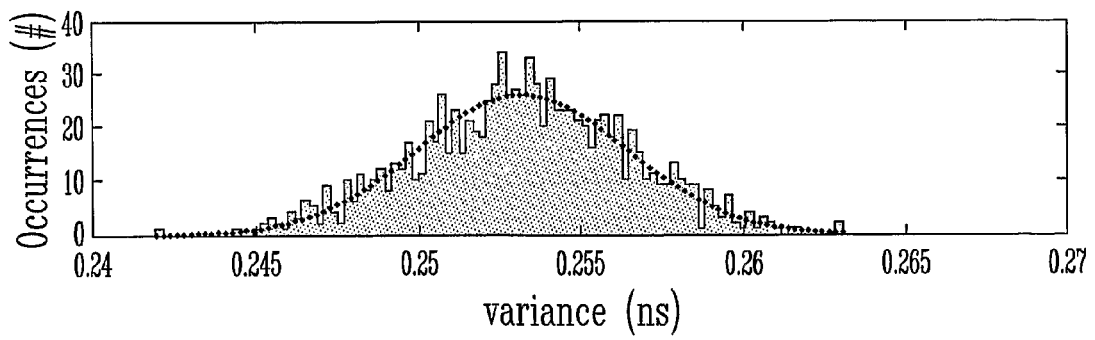
Figure 12A:
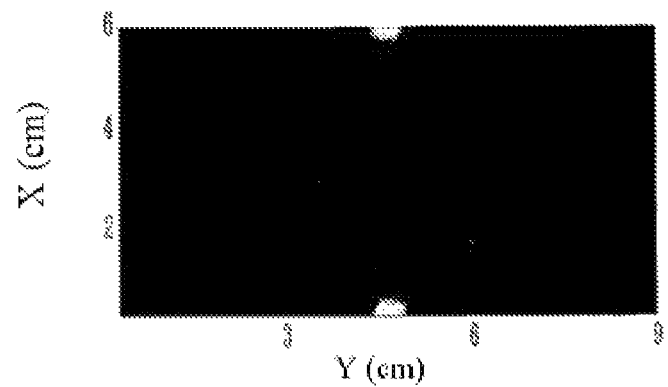
FIG. 12 is an example of sensitivity matrices in which a) and b) correspond respectively to $m_0^{\lambda_2}(r_s, r_d)$ and $m_2^{\lambda_2}(r_s, r_d) \cdot m_0^{\lambda_2}(r_s, r_d)$ for a 6 cm thick slab with source-detector facing each other and a 0.1 μM background of Cy 7, c) and d) correspond to the same parameters for a 0.1 μM background of Cy 5.5 and e) and f) correspond to the same parameters for a 0.1 μM background of Cy 3B.
Figure 12B:
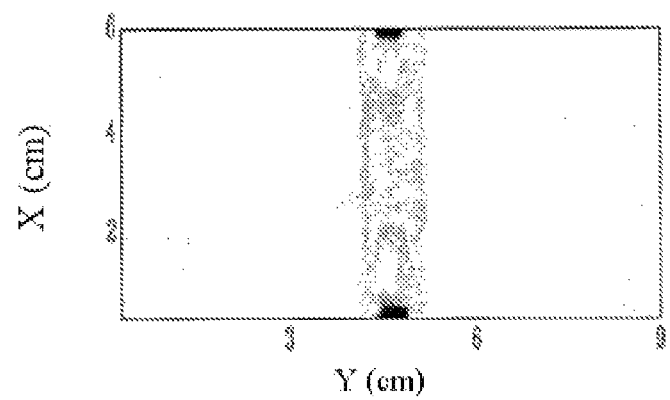
Figure 12C:
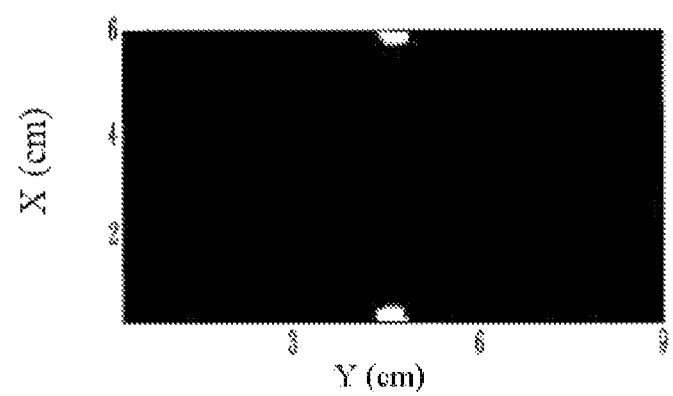
Figure 12D:
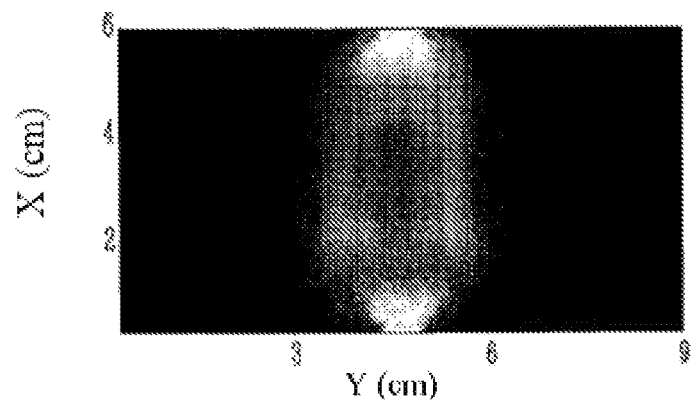
Figure 12E:
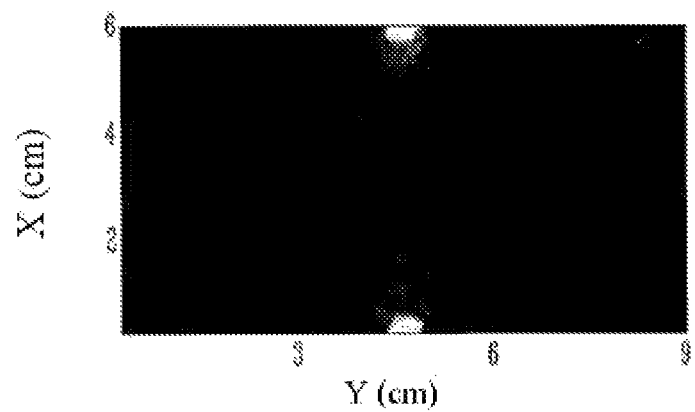
Figure 12F:
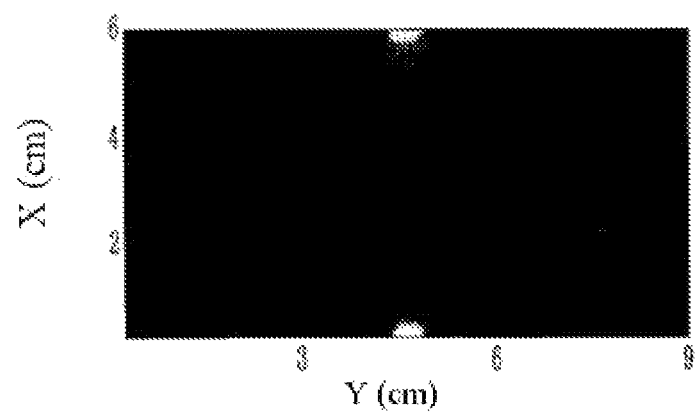

We generated synthetic homogeneous TPSF and considered a Poisson noise of the temporal distribution of photon time of flights. The TPSF was normalized at 500 counts at the maximum bin mimicking real acquisition scenarios. From the noised TPSF, we estimated one set of energy, meantime and variance. The same estimation was performed over 1,000 trials. The statistics of these estimates were used as our noise model. An example of noisy moments value distribution is given in FIG. 11.

A Gaussian distribution approximated the noise model. The different values of the noise model employed for the three moments evaluated herein are Measure σ (%), Energy: 2, Meantime: 0.2, and Variance: 2.

We propose in FIG. 12 some examples of sensitivity matrices for the transmittance case. We limited ourselves to depict slices across the discrete volume, but by construction, the banana shapes are in 3D. The optical and fluorochrome properties characterizing this medium are provided in Table 2 and Table 3.

The examples in FIG. 12 underline interesting features of the time domain moment fluorescent DOT. First, as seen in FIGS. 12 a)-c) and e), the normalized $0^{th}$ order Born approximation in continuous mode is highly sensitive to surface voxels.

Secondly, we see that the spatial dependence profile of the $2^{nd}$ normalized fluorescent moment possesses distinctive features. The $2^{nd}$ normalized fluorescent moment still exhibits some strong dependence from the surface voxels, but also from deeper voxels. The profile presents a distinguishing depression in the line connecting the source-detector pair. This fact is striking in the case of FIG. 12 d) where we used the properties of Cy 7 for the simulated chromophore. In this specific case, the $2^{nd}$ normalized fluorescent moment is characterized by a sharp and well-demarcated hollow dependence. Such typical features are related to the fact that the fluorescent mean time $\bar{t}^{\lambda 2}(r_s, r_d)$ is subtracted in Eq (11). Indeed, the measured mean-time is always greater than the mean time of propagation for the shorter path, i.e. for the voxels located on the line connecting the source-detector pair. Then if the contribution of the lifetime is small enough, the $2^{nd}$ normalized fluorescent moment will exhibit reduced (eventually negative) contribution for these voxels. This property is dependent on the lifetime of the fluorochrome investigated. This hollow distribution is still present for the Cy 5.5 case but disappears for the Cy 3B simulations. In this last case, the contribution of the lifetime is predominant for these shorter path voxels and the spatial distribution of $2^{nd}$ normalized fluorescent moment is not markedly different than the $0^{th}$ normalized fluorescent moment.

Figures 13A, 13B, 13C:
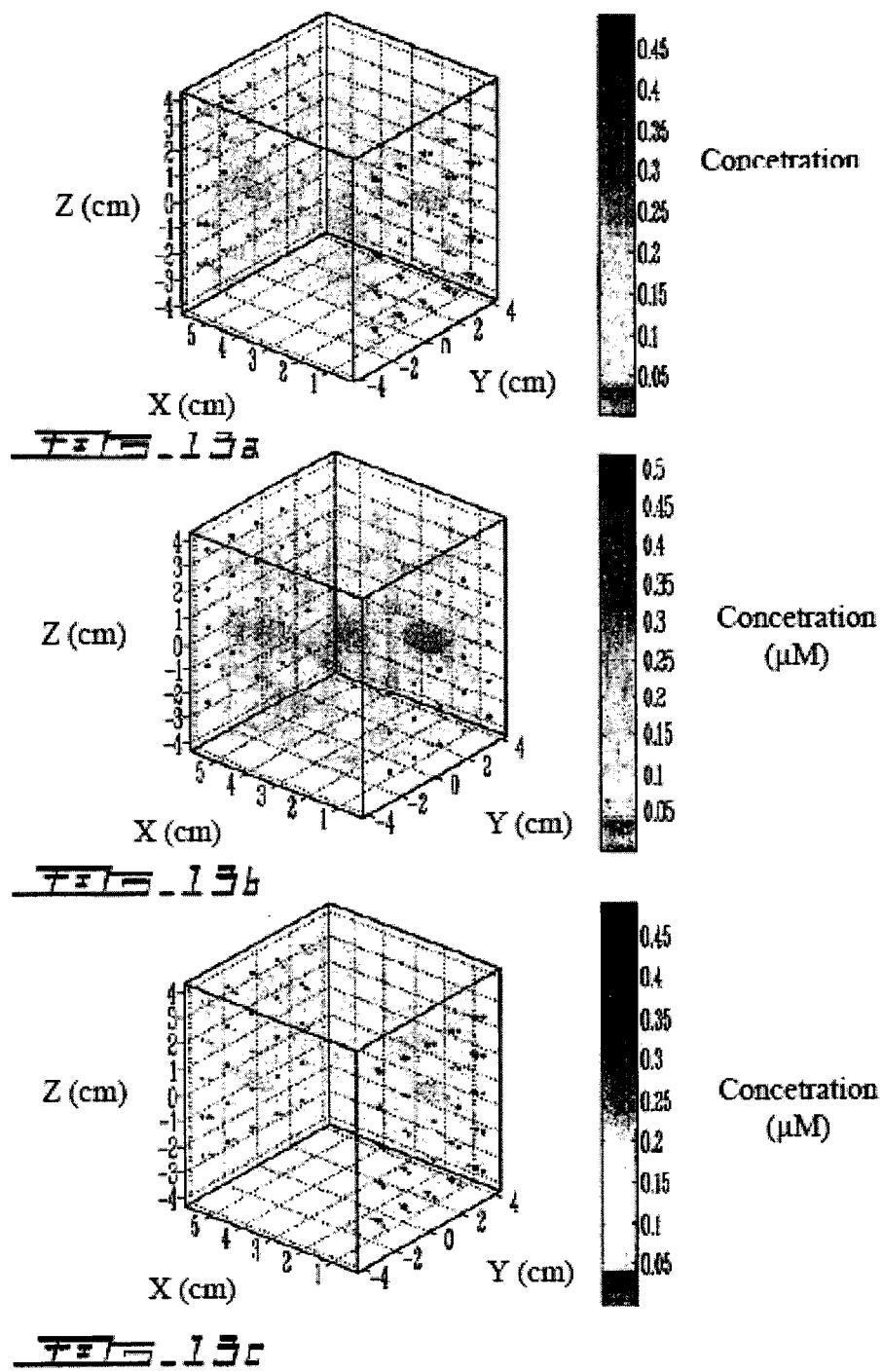
FIG. 13. is an example of a reconstruction from synthetic data for Cy 7: a) $0^{th}$ moment only, b) $0^{th}$, $1^{st}$ and $2^{nd}$ moments; Cy 5.5: c) $0^{th}$ moment only, d) $0^{th}$, $1^{st}$ and $2^{nd}$ moments; and Cy 3B: e) $0^{th}$ moment only, f) $0^{th}$, $1^{st}$ and $2^{nd}$ moments in which the quantitative values are expressed in μM.
Figures 13D, 13E, 13F:
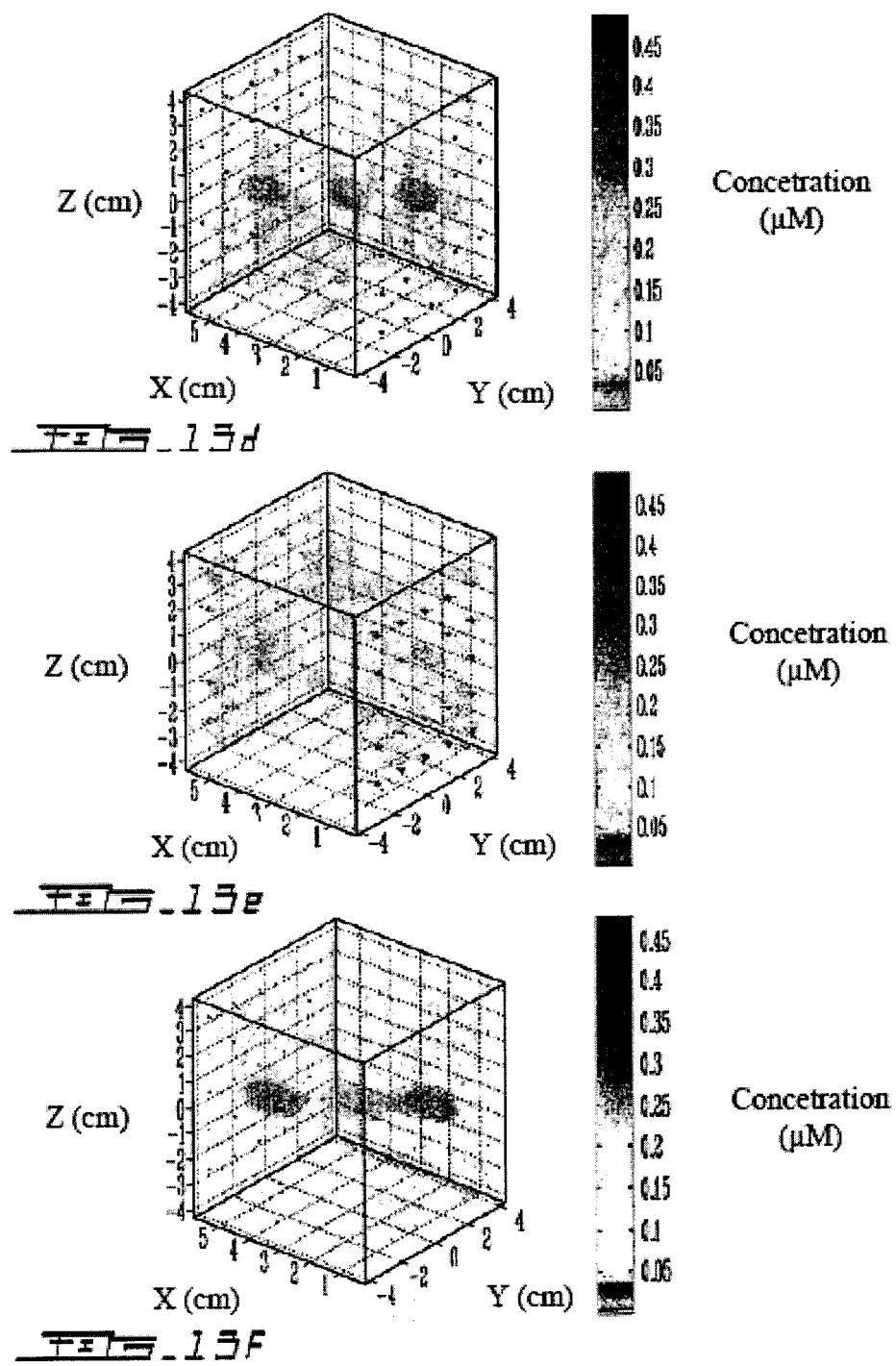

One should note that the background fluorochrome concentration is non-negligible. This background simulates non-perfect compound uptake/trapping and represents a challenging case for all FDOT approaches. We use then the formulation of equation (12) to generate synthetic measurements from the phantom. We simulated a 25 sources and 25 detectors array. The value of the fluorescent mean time and the fluorescent variance were evaluated to be around ~3 ns and 1 ns respectively. These values are in agreement with expected values for real cases. In this simulation no noise was added. The reconstructions obtained by constrained ART are provided in FIG. 13. We propose in this figure the reconstructions based on the $0^{th}$ normalized moment of the fluorescent TPSF and with the combined three normalized moments. In all three cases presented, the inclusions were successfully reconstructed. Their locations were well retrieved and the objects clearly discriminated from the background. However, we can notice some differences in terms of reconstruction quality between the three different inverse problems solved. Especially, in the case using only the $0^{th}$ normalized moment of the fluorescent TPSF, the reconstructions exhibit strong artifacts on the boundary, artifacts that scale with the reconstructed heterogeneity. On the other hand the reconstructions based on the three moments combined (as reconstructions based on the $2^{nd}$ normalized fluorescent moment solely; results not shown here) do not exhibit such strong surface artifacts. In this last case, the homogenous background fluorophore is more accurately reconstructed.

For the $0^{th}$ normalized moment reconstructions, a high sensitivity to surface voxels leads to artifacts placed in front of the individual sources and detectors. This is emphasized in our case where a non-negligible fluorophore homogeneous background concentration was simulated. The contribution of this homogenous background to the measurements is reconstructed as strong concentrations localized in front of the optodes. Reconstructions based on the $2^{nd}$ normalized fluorescent moment suffer less from this ambiguity. In the latter case, the reconstruction does not exhibit artifact scaling with the reconstructed heterogeneity and the homogeneous background is reconstructed with more fidelity. The gain is even more substantial when the three moments are used simultaneously in the inverse problem. In this case, the object is accurately reconstructed in location and size with a more homogeneous background fluorophore concentration.

Last, the reconstructions based on the three different compounds are very similar when using only the $0^{th}$ normalized moment. However, the reconstructions employing the $2^{nd}$ normalized moment exhibit different performances. In the case of relatively short lifetimes, i.e. Cy 7 and Cy 5.5, the reconstructions are similar and provide accurate recovery of the three heterogeneities. However, in the case of longer lifetime, i.e. Cy 3B, even though, the reconstructions are far superior when using the 3 moments simultaneously in the inverse problem, the objects are less well defined. This fact is linked to the close similarity between the spatial distributions of the $0^{th}$ normalized and the $2^{nd}$ normalized fluorescent moments. One should note also that the constellation of source-detector selected herein is quite sparse and such reconstructed structure is expected as seen in ref Graves et al. J. Opt. Soc. Am. A 21, 231-241 (2004).

Figure 14:
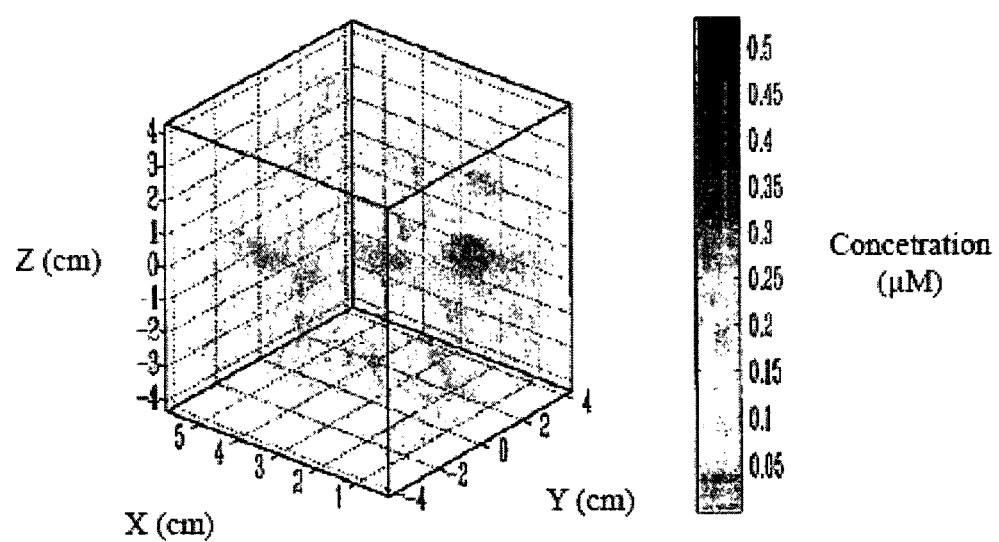
FIG. 14 is an example of a reconstruction from synthetic data for Cy 5.5 using all three moments noisy data.

The noise model described above was applied to the measurements for the Cy 5.5 case. The reconstructions based on this noisy simulation are provided in FIG. 14. We restricted the reconstruction to the Cy 5.5 case only for conciseness.

As one can see, the algorithm is still performing satisfactorily in the case of noise. Even though the $2^{nd}$ normalized moments are sensitive to noise, the incorporation of this information benefits the inverse problem. The objects are reconstructed with fidelity and the surface artifacts are still minimized due to the inherent spatial information of the $2^{nd}$ normalized moment.

REFERENCES

[1] Yodh A G, Chance B. Spectroscopy and imaging with diffusing light. Physics Today (1995); 48:34-40.
[2] Jobsis F. Noninvasive infrared monitoring of cerebral and myocardial sufficiency and circulatory parameters. Science (1977); 198:1264-67.
[3] Tromberg B, Shah N, Lanning R, Cerussi A, Espinoza J, Pham T, et al. Non-invasive in vivo characterization of breast tumors using photon migration spectroscopy. Neoplasia (2000); 2:26-40.
[4] Dehghani, H., Pogue, B. W., Poplack, S. P., Paulsen, K. D., "Multiwavelength three-dimensional near-infrared tomography of the breast: initial simulation, phantom, and clinical results", Applied Optics, 42(1) 135-145, 2003.
[5] Jiang H, Iftimia N, Eggert J, Fajardo L, Klove K. Near-infrared optical imaging of the breast with model-based reconstruction. Acad. Radiology (2002); 9:186-94.
[6] Franceschini M, Moesta K, Fantini S, Gaida G, Gratton E, Jess H et al. Frequency-domain techniques enhance optical mammography: Initial clinical results. PNAS (1997); 94:6468-73.
[7] Colak S, van der Mark M, Hooft G, Hoogenraad J, van der Linden E, Kuijpers F. Clinical optical tomography and NIR spectroscopy for breast cancer detection. IEEE Journal of selected topics in quantum electronics (1999); 5:1143-58.
[8] Intes X, Djeziri S, Ichalalene Z, Mincu N, Wang Y, Kasrai R, Polyzos M, Hall D, Boas D, St-Jean P, Lesage F, Khayat M. Time-Domain Optical Mammography Softscan®: Initial Results on Detection and Characterization of Breast Tumors. In the same proceedings.
[9] Jakubowski D B, Cerussi A E, Bevilacqua F, Shah N, Hsiang D, Butler J, Tromberg B J. Monitoring neoadjuvant chemotherapy in breast cancer using quantitative diffuse optical spectroscopy: a case study. J Biomed Opt. (2004); 9:230-238.
[10] Strangman G, Boas D, Sutton J. Non-invasive neuroimaging using Near-Infrared light. Biol. Psychiatry (2002); 52:679-93.
[11] Villringer A, Chance B. Non-invasive optical spectroscopy and imaging of human brain function. Trends Neurosci. (1997); 20:435-42.
[12] Chance B, Nioka S, Chen Y. Shining new light on brain function. OE magazine (2003); 3:16-9.
[13] Steinbrink J, Kohl M, Obrig H, Curio G, Syre F, Thomas F, et al. Somatosensory evoked fast optical intensity changes detected non-invasively in the adult human head. Neuroscience Letters (2000); 291:105-8.
[14] Stankovic M, Maulik D, Rosenfeld W, Stubblefield P, Kofinas A, Gratton E, et al. Role of frequency domain optical spectroscopy in the detection of neonatal brain hemorrhage—a newborn piglet study. J. Matern Fetal Med. (2000); 9:142-9.

[15] Hebden J C, Gibson A, Austin T, Yusof R M, Everdell N, Delpy D T, Arridge S R, Meek J H, Wyatt J S. Imaging changes in blood volume and oxygenation in the newborn infant brain using three-dimensional optical tomography. Phys Med Biol. (2004); 49:1117-1130.

[16] Quaresima V, Lepanto R, Ferrari M. The use of near infrared spectroscopy in sports medicine. J Sports Med Phys Fitness (2003); 43:1-13.

[17] Wolf U, Wolf M, Choi J, Levi M, Choudhury D, Hull S, et al. Localized irregularities in hemoglobin flow and oxygenation in calf muscle in patients with peripheral vascular disease detected with near-infrared spectrophotometry. Vasc Surg. (2003); 37:1017-26.

[18] Weissleder R and Mahmood U. Molecular imaging. Radiology. 2001 May; 219(2):316-33.

[19] Weissleder R, Ntziachritos V. Shedding light onto live molecular targets. Nature Medicine (2003); 9:123-8.

[20] Frangioni J V. In vivo near-infrared fluorescence imaging. Current Opinion in Chemical Biology (2003); 7:626-34.

[21] Licha K. Contrast agents for optical imaging. Topics in Current Chemistry (2002); 222: 1-29.

[22] Achilefu S, Dorshow R, Bugaj J, Rajagopalan R. Novel receptor-targeted fluorescent contrast agents for in-vivo tumor imaging. Invest. Radiol. (2000); 35:479-85.

[23] Chen Y, Zheng G, Zhang Z, Blessington D, Zhang M, H. Li, et al. Metabolism Enhanced Tumor Localization by Fluorescence Imaging: In Vivo Animal Studies. Optics Letters (2003); 28:2070-2.

[24] Weissleder R, Tung C H, Mahmood U, Bogdanov A. In vivo imaging with protease-activated near-infrared fluorescent probes. Nat. Biotech. (1999); 17:375-8.

[25] Weinberg R. How Does Cancer Arise. Sci. Am. (1996); 275:62-71.

[26] Lewis J, Achilefu S, Garbow J R, Laforest R, Welch M J. Small animal imaging: current technology and perspectives for oncological imaging. European Journal of Cancer (2002); 38:2173-88.

[27] Ntziachristos V, Ripoll J, Weissleder R. Would near-infrared fluorescence signals propagate through large human organs for clinical studies? Opt. Lett. (2002); 27:333-335.

[28] Ntziachristos V, Weissleder R. Experimental three-dimensional fluorescence reconstruction of diffuse media by use of a normalized Born approximation. Opt. Lett. (2001); 26:893-895.

[29] Eppstein M J, Hawrysz D J, Godavarty A, Sevick-Muraca E M. Three-dimensional, Bayesian image reconstruction from sparse and noisy data sets: Near-infrared fluorescence tomography. Proc. Nat. Acad. Sci. Am. (2002); 99: 9619-9624.

[30] Milstein A B, Stott J J, Oh S, Boas D A, Millane R P, Bouman C A, Webb K J. Fluorescence optical diffusion tomography using multiple-frequency data. J. Opt. Soc. Am. A (2004); 21: 1035-1049.

[31] Xingde Li. Fluorescence and diffusive wave diffraction tomographic probes in turbid media PhD University of Pennsylvania (1996).

[32] O'Leary M. Imaging with diffuse photon density waves. PhD University of Pennsylvania (1996).

[33] Hillman E. Experimental and theoretical investigations of near infrared tomographic imaging methods and clinical applications. PhD University College London (2002).

[34] Liebert A, Wabnitz H, Grosenick D, Moller M, Macdonald R and Rinnerberg H. Evaluation of optical properties of highly scattering media by moments of distributions of times of flight of photons. Appl. Opt. (2003); 42:5785-5792.

[35] Haskell R C, Svaasand L O, Tsay T, Feng T, McAdams M S, Tromberg B J. Boundary conditions for the diffusion equation in radiative transfer. J. Opt. Soc. Am A (1994); 11; 2727-41.

[36] Gaudette R J, Brooks D H, DiMarzio C A, Kilmer M E, Miller E L, Gaudette T. Boas D A. A comparison study of linear reconstruction techniques for diffuse optical tomographic imaging of absorption coefficient. Phys Med Biol. (2000); 45:1051-1070.

[37] Gordon R, Bender R and Herman G Algebraic reconstruction techniques (ART) for the three dimensional electron microscopy and X-Ray photography. J. Theoret. Biol. (1970); 69:471-482.

[38] Kak A and Slaney M, "Computerized tomographic Imaging", IEE Press, N-Y (1987).

[39] Ros D, Falcon C, Juvells I and Pavia J. The influence of a relaxation parameter on SPECT iterative reconstruction algorithms Phys. Med. Biol. (1996); 41: 925-937.

[40] Herman G & Meyer L. Algebraic Reconstruction Techniques can be made computationally efficient. IEEE Transactions on Medical Imaging (1993); 12:600-609.

[41] Gaudette R, Brook D, DiMarzio C, Kilmer M, Miller E, Gaudette T & Boas D. A comparison study of linear reconstruction techniques for diffuse optical tomographic imaging of absorption coefficient. Phys. Med. Biol. (2000); 45:1051-1070.

[42] van der Sluis A and van der Vorst H. SIRT- and CG-type methods for the iterative solution of sparse linear least-squares problems. Linear Algebr. Appl. (1990); 130:257-302.

[43] Intes X, Ntziachristos V, Culver J, Yodh A G and Chance B. Projection access order in Algebraic Reconstruction Techniques for Diffuse Optical Tomography. Phys. Med. Biol. (2002); 47:N1-N10.

The embodiment(s) of the invention described above is (are) intended to be exemplary only. The scope of the invention is therefore intended to be limited solely by the scope of the appended claims.

We claim:

1. A method for determining a concentration of a fluorophore in a medium as a function of three spatial coordinates of a three dimensional frame of reference, said method comprising:
   acquiring fluorescence-based measurements from three or more source-detector pairs;
   obtaining, for each source-detector pair, a moment of order k from fluorescence-based measurements acquired at that source-detector pair; and
   determining said concentration as a function of said three spatial coordinates based on said moments of order k and on a weighting coefficient for each source-detector pair.

2. The method as claimed in claim 1 wherein said fluorescence-based measurements are described by a photon diffusion equation and wherein said weighting coefficient is based on said photon diffusion equation.

3. The method as claimed in claim 2 wherein said photon diffusion equation is a normalized first order fluorescent Born approximation equation.

4. The method as claimed in claim 3 wherein said fluorescence-based photon diffusion equation is a time-domain photon diffusion equation and wherein said measurements define a temporal point spread function (TPSF).

5. The method as claimed in claim 1 wherein said moments are selected from 0, $1^{st}$, $2^{nd}$ moments and combinations thereof.

6. The method as claimed in claim 5 wherein said moments are normalized moments.

7. The method as claimed in claim 1 wherein one of said three spatial coordinates represents depth relative to a surface of said medium.

8. The method as claimed in claim 1 wherein said medium is a biological tissue.

9. The method as claimed in claim 8 wherein said biological tissue is selected from brain tissue and breast tissue.

10. The method as claimed in claim 8 wherein said fluorophore is an endogenous fluorophore.

11. The method as claimed in claim 8 wherein said fluorophore is an exogenous fluorophore.

* * * * *